United States Patent
Josso et al.

(12) 
(10) Patent No.: US 6,372,200 B2
(45) Date of Patent: Apr. 16, 2002

(54) UV-PHOTOPROTECTING SUNSCREEN COMPOSITIONS COMPRISING IMMIXTURE OF POLYETHYLENE/CARBOXYLATED POLYETHYLENE POLYMERS

(75) Inventors: Martin Josso, Paris; Stéphanie Meurisse, St Prix, both of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/771,661

(22) Filed: Jan. 30, 2001

(30) Foreign Application Priority Data

Feb. 8, 2000 (FR) .............................. 00 01535

(51) Int. Cl.[7] .............................. A61K 7/42; A61K 7/44; A61K 31/74; A61K 7/00
(52) U.S. Cl. ..................... 424/59; 424/60; 424/78.02; 424/78.08; 424/400; 424/401
(58) Field of Search ................... 424/59, 60, 78.02, 424/78.08, 400, 401

(56) References Cited

U.S. PATENT DOCUMENTS

| | | |
|---|---|---|
| 5,208,011 A | 5/1993 | Vaughan |
| 5,250,289 A | 10/1993 | Boothroyd et al. |
| 5,417,961 A | 5/1995 | Nearn et al. |
| 5,770,183 A | 6/1998 | Linares |
| 6,007,797 A | 12/1999 | Bell et al. |

FOREIGN PATENT DOCUMENTS

| WO | WO 97/12584 | 4/1997 |
|---|---|---|
| WO | WO 97/42933 | 11/1997 |
| WO | WO 98/46200 | 10/1998 |

OTHER PUBLICATIONS

Japanese Abstract JP 61 257910, XP002157184, Nov. 15, 1986, Derwent Publications Ltd., London, GB.

Japanese Abstract JP 10 273433 A, XP002157185, Oct. 13, 1998, Derwent Publications, Ltd., London, GB.

Japanese Abstract JP 08 310941 A, XP002157186, Nov. 26, 1996, Derwent Publications, Ltd., London, GB.

"SPF Waterproof W/O Emulsion", Happi Magazine—Formulary/Mar. 2000, XP002157182, Jan. 11, 2001.

McCullough & Benton, "Personal Care Industry", XP002157183.

*Primary Examiner*—Shelley A. Dodson
(74) *Attorney, Agent, or Firm*—Burns, Doane, Swecker & Mathis, L.L.P.

(57) ABSTRACT

Topically applying cosmetic/dermatological compositions well suited for both effective and SPF-enhanced UV-photoprotection of human skin and/or hair contain (a) an effective UV-photoprotecting amount of at least one UV-A and/or UV-B sunscreen and (b) an amount of immixture of ethylene polymers effective to enhance the SPF value of said at least one UV-A and/or UV-B sunscreen (a), said immixture of ethylene polymers (b) comprising (i) at least one carboxylated polyethylene and (ii) at least one polyethylene, formulated into a topically applicable, cosmetically/dermatologically acceptable vehicle, diluent or carrier therefor, advantageously formulated as an oil-in-water emulsion.

26 Claims, No Drawings

UV-PHOTOPROTECTING SUNSCREEN COMPOSITIONS COMPRISING IMMIXTURE OF POLYETHYLENE/CARBOXYLATED POLYETHYLENE POLYMERS

CROSS-REFERENCE TO PRIORITY APPLICATION

This application claims priority under 35 U.S.C. § 119 of FR-00/01535, filed Feb. 8, 2000, hereby expressly incorporated by reference.

BACKGROUND OF THE INVENTION

Technical Field of the Invention

The present invention relates to novel cosmetic/dermatological compositions for topical application, for the ultraviolet (UV)-photoprotection of the skin and/or the hair against the damaging effects of UV radiation, in particular solar radiation, comprising, formulated into a cosmetically and/or dermatologically acceptable support therefor (vehicle, diluent or carrier), at least one sunscreen system effective for screening out UV radiation and at least one mixture of polyethylene polymers including at least one polyethylene containing a carboxylic acid end function in free, partially neutralized or totally neutralized form and at least one polyethylene.

The present invention also relates to formulating a mixture of polyethylene polymers including at least one polyethylene containing a carboxylic acid end function in free, partially neutralized or totally neutralized state and at least one polyethylene into cosmetic and/or dermatological compositions suited for protecting human skin and/or hair against the damaging effects of UV radiation, in particular solar radiation, and enhancing the sun protection factors (SPF) thereof.

Description of the Invention

It is known to this art that light radiation of wavelengths of from 280 nm and 400 nm promotes tanning of the human epidermis and that irradiation of wavelengths of from 280 nm and 320 nm, i.e., UV-B irradiation, causes skin burns and erythema which may be harmful to the development of a natural tan; this UV-B radiation should thus be screened from the skin.

It is also known to this art that UV-A radiation, of wavelengths of from 320 nm and 400 nm, which causes tanning of the skin, also adversely affects it, especially in the case of sensitive skin or skin which is continually exposed to solar radiation. In particular, UV-A rays cause a loss of elasticity of the skin and the appearance of wrinkles, promoting premature skin aging. Such irradiation promotes triggering of the erythemal reaction or amplifies this reaction in certain individuals and may even be the cause of phototoxic or photoallergic reactions. It is thus desirable to also screen out UV-A radiation.

A wide variety of cosmetic compositions intended for the sunscreen (UV-A and/or UV-B) protection of the skin is known to this art.

These antisun/sunscreen compositions are quite often in the form of an emulsion of oil-in-water type (i.e., a cosmetically acceptable support comprising a continuous aqueous dispersing phase and a discontinuous oil dispersed phase) which contains, in varying concentrations, one or more conventional lipophilic and/or hydrophilic organic screening agents which are capable of selectively absorbing harmful UV radiation, these screening agents (and the amounts thereof) being selected as a function of the desired sun protection factor (the sun protection factor (SPF) being expressed mathematically as the ratio of the irradiation time required to attain the erythema-forming threshold with the UV-screening agent to the time required to attain the erythema-forming threshold in the absence of UV-screening agent).

SUMMARY OF THE INVENTION

It has now surprisingly and unexpectedly been determined that by formulating into appropriate medium or support, for example an oil-in-water emulsion, a specific intimate immixture of polyethylenes with an effective sunscreen system, antisun/sunscreen compositions are provided that have higher sun protection factors than those comprising the same sunscreen system alone.

Thus, the present invention features novel compositions for effectively photoprotecting the skin and/or the hair against the damaging effects of ultraviolet radiation, comprising, and formulated into a topically applicable, cosmetically/dermatologically acceptable vehicle, diluent or carrier therefor, most advantageously an oil-in-water emulsion:

(a) at least one sunscreen system effective for screening out UV radiation;

(b) at least one mixture of polyethylene polymers which comprises at least one polyethylene containing a carboxylic acid end function and at least one polyethylene.

DETAILED DESCRIPTION OF BEST MODE AND SPECIFIC/PREFERRED EMBODIMENTS OF THE INVENTION

More particularly according to the present invention, by the expression "sunscreen system effective for screening out UV radiation" is intended any compound or any combination of compounds which, by mechanisms that are known per se of absorption and/or reflection and/or scattering of UV-A and/or UV-B radiation, prevents, or at least limits, the contact between such radiation and a surface (skin, hair) on which this or these compounds have been applied. Stated differently, these compounds may be UV-absorbing organic sunscreen screening agents or inorganic (nano)pigments which scatter and/or reflect UV, as well as mixtures thereof.

The present invention thus also features formulating a mixture of polyethylenes which includes at least one polyethylene containing a carboxylic acid endgroup and at least one polyethylene, into compositions suited for protecting the skin and/or the hair against the damaging effects of ultraviolet radiation, such compositions most preferably comprising oil-in-water emulsions and also including a sunscreen system suited for screening out UV radiation and having enhanced sun protection factors (SPF).

The polyethylene mixtures in accordance with the present invention generally comprise from 60% to 99% by weight and more preferably from 80% to 90% by weight of a polyethylene containing a carboxylic acid endgroup and from 1% to 40% by weight and more preferably from 10% to 20% by weight of a polyethylene, per se, both relative to the total weight of the mixture.

In the polyethylene mixtures of this invention, the carboxylic acid endgroup may optionally be partially neutralized or totally neutralized with a mineral base such as sodium hydroxide, potassium hydroxide or aqueous ammonia or an organic base such as an amine or an alkanolamine such as triethanolamine.

The polyethylene mixtures in accordance with the present invention preferably have a number-average molecular weight ranging from 300 to 800, an acid number ranging from 60 to 120 and a melting point ranging from 80° C. to 120° C.

Among the polyethylene mixtures according to this invention which are more particularly preferred are the products marketed under the trademark "Performacid" by New Phase Technologies, such as, for example:

(1) the mixture of polyethylene containing a carboxylic acid end function/polyethylene of molecular weight 350, of acid number 115 and of melting point 89° C. (INCI name: $C_{20}$–$C_{40}$ Acid and Polyethylene) marketed under the trademark "Performacid 350";

(2) the mixture of polyethylene containing a carboxylic acid end function/polyethylene of molecular weight 460, of acid number 94 and of melting point 94° C., marketed under the trademark "Performacid 425";

(3) the mixture of polyethylene containing a carboxylic acid end function/polyethylene of molecular weight 550, of acid number 72.5 and of melting point 101° C., marketed under the trademark "Performacid 550";

(4) the mixture of polyethylene containing a carboxylic acid end function/polyethylene of molecular weight 700, of acid number 63 and of melting point 110° C., marketed under the trademark "Performacid 700".

The polyethylene mixtures of the invention are advantageously formulated into the subject compositions at concentrations preferably ranging from 0.1% to 10% by weight relative to the total weight of the composition and more preferably from 0.2% to 5% by weight.

The sunscreen system according to the invention is generally present in the subject compositions at a content ranging from 0.1% to 30% by weight and preferably from 0.5% to 15% by weight relative to the total weight of the composition.

According to the invention, the sunscreen system may comprise one or more hydrophilic organic screening agents and/or one or more lipophilic organic screening agents and/or one or more mineral or inorganic (nano)pigments.

The hydrophilic or lipophilic UV-A-active and/or UV-B-active organic screening agents are advantageously selected, in particular, from among the cinnamic derivatives; dibenzoylmethane derivatives; salicylic derivatives; camphor derivatives; triazine derivatives such as those described in U.S. Pat. No. 4,367,390, EP-A-0 863 145, EP-A-0 517 104, EP-A-0 570 838, EP-A-0 796 851, EP-A-0 775 698, EP-A-0 878 469 and EP-A-0 933 376; benzophenone derivatives; β,β'-diphenylacrylate derivatives; benzimidazole derivatives; bis-benzazolyl derivatives such as those described in EP-A-0 669 323 and U.S. Pat. No. 2,463,264; bis-hydroxyphenolbenzotriazole derivatives such as those described in U.S. Pat. Nos. 5,237,071 and 5,166,355, GB-A-2 303 549, DE 19726184 and EP-A-0 893 119; p-aminobenzoic acid derivatives; screening hydrocarbon-based polymers and screening silicones such as those described, in particular, in WO-93/04665.

Exemplary hydrophilic or lipophilic UV-A-active and/or UV-B-active organic screening agents which are representative include:

p-aminobenzoic acid,
oxyethylenated (25 mol) p-aminobenzoate,
2-ethylhexyl p-dimethylaminobenzoate,
N-oxypropylenated ethyl p-aminobenzoate,
glyceryl p-aminobenzoate,
homomenthyl salicylate,
2-ethylhexyl salicylate,
triethanolamine salicylate,
4-isopropylbenzyl salicylate,
4-tert-butyl-4'-methoxydibenzoylmethane,
4-isopropyldibenzoylmethane,
2-ethylhexyl 4-methoxycinnamate,
methyl diisopropylcinnamate,
isoamyl 4-methoxycinnamate,
diethanolamine 4-methoxycinnamate,
menthyl anthranilate,
2-ethylhexyl 2-cyano-3,3'-diphenylacrylate,
ethyl 2-cyano-3,3'-diphenylacrylate,
2-phenylbenzimidazole-5-sulfonic acid and salts thereof,
3-(4'-trimethylammonium)benzylidenebornan-2-one methyl sulfate,
2-hydroxy-4-methoxybenzophenone,
2-hydroxy-4-methoxybenzophenone 5-sulfonate,
2,4-dihydroxybenzophenone,
2,2',4,4'-tetrahydroxybenzophenone,
2,2'-dihydroxy-4,4'-dimethoxybenzophenone,
2-hydroxy-4-n-octoxybenzophenone,
2-hydroxy-4-methoxy-4'-methylbenzophenone,
4-α-(2-oxoborn-3-ylidene)tolylsulfonic acid and soluble salts thereof,
3-(4'-sulfo)benzylidenebornan-2-one and soluble salts thereof,
3-(4'-methylbenzylidene)-d,l-camphor,
3-benzylidene-d,l-camphor,
benzene-1,4-bis(3-methylidene-10-camphorsulfonic acid) and soluble salts thereof,
urocanic acid,
2,4,6-tris[p-(2'-ethylhexyl-1'-oxycarbonyl)anilino]-1,3,5-triazine,
2-[p-(tert-butylamido)anilino]-4,6-bis[(p-(2'-ethyl-hexyl-1'-oxycarbonyl)anilino]-1,3,5-triazine,
2,4-bis{[4-(2-ethylhexyloxy)]-2-hydroxy]phenyl}-6-(4-methoxyphenyl)-1,3,5-triazine,
the polymer of N-(2 and 4)-[(2-oxoborn-3-ylidene)-methyl]benzyl]acrylamide,
1,4-bis(benzimidazolyl)phenylene-3,3',5,5'-tetra-sulfonic acid and soluble salts thereof,
2,2'-methylenebis[6-(2H-benzotriazol-2-yl)-4-(1,1,3,3-tetramethylbutyl)phenol],
the compound (2,2'-methylenebis[6-(2H-benzotriazol-2-yl)-4-(methyl)phenol],
polyorganosiloxanes containing a benzalmalonate function,
polyorganosiloxanes containing a benzotriazole function such as drometrizole trisiloxane.

Exemplary hydrophilic organic screening agents well suited for formulation into the compositions of the present invention include benzene-1,4-bis(3-methylidene-10-camphorsulfonic acid) marketed under the trademark "Mexoryl SX" by Chimex and 2-phenylbenzimidazole-5-sulfonic acid marketed under the trademark "Eusolex 232" by the company Merck.

And exemplary lipophilic organic screening agents according to the present invention include:

4-tert-butyl-4'-methoxydibenzoylmethane marketed under the trademark "Parsol 1789" by Hoffmann Laroche;

octyl methoxycinnamate marketed under the trademark "Parsol MCX" by Hoffmann Laroche;

2-ethylhexyl α-cyano-β,β-diphenylacrylate (octocrylene) marketed under the trademark "Uvinul N 539" by BASF;

4-methylbenzylidenecamphor marketed under the trademark "Eusolex 6300" by Merck;

benzophenone-3 (oxybenzone) marketed under the trademark "Uvinul M40" by BASF;

2-ethylhexyl salicylate or octyl salicylate marketed under the trademark Neo Heliopan OS by Haarmann & Reimer;

2,4,6-tris[p-(2'-ethylhexyl-1'-oxycarbonyl]-anilino]-1,3,5-triazine marketed under the trademark "Uvinul T 150" by BASF;

drometrizole trisiloxane marketed under the trademark "Silatrizole" by Rhodia Chimie.

A second category of additional sunscreen agents which may be formulated into the compositions of this invention is that of pigments. Preferably, mineral or inorganic nanopigments (average size of the primary particles: generally between 5 nm and 100 nm, preferably between 10 nm and 50 nm) of coated or uncoated metal oxides such as, for example, nanopigments of titanium dioxide (amorphous or crystallized in rutile and/or anatase state), of iron oxide, of zinc oxide, of zirconium oxide or of cerium oxide are formulated, which are all sunscreen agents that are well known per se which act by physically blocking out (reflection and/or scattering) UV radiation. Conventional coating agents are, moreover, alumina and/or aluminum stearate or silicones. Such coated or uncoated metal oxide nanopigments are described, in particular, in EP-A-0 518 772 and EP-A-0 518 773.

The mineral (nano)pigment(s) are advantageously present in the compositions according to the invention in a content of from 0.1% to 30%, preferably from 0.5% to 10%, by weight relative to the total weight of the composition.

The compositions according to the invention may also contain agents for artificially or sunless tanning and/or bronzing the skin (self-tanning agents) such as, for example, dihydroxyacetone (DHA).

The compositions of this invention may also comprise conventional cosmetic additives and adjuvants selected, in particular, from among fatty substances, organic solvents, thickeners, softeners, opacifiers, stabilizers, colorants, emollients, antifoams, moisturizers, fragrances, preservatives, polymers, fillers, sequestering agents, bactericides and/or odor absorbers, acidifying or basifying agents, surfactants, free-radical scavengers, antioxidants, vitamins such as vitamins E and C, α-hydroxy acids or any other ingredient conventionally formulated into cosmetics, in particular for the manufacture of antisun/sunless compositions in the form of emulsions.

Exemplary fatty substances include an oil or a wax or mixtures thereof and they can also comprise fatty acids, fatty alcohols and fatty acid esters. The oils are advantageously selected from among animal, plant, mineral and synthetic oils and, in particular, from among liquid petroleum jelly, liquid paraffin, volatile or non-volatile silicone oils, isoparaffins, polyolefins, fluoro oils and perfluoro oils. Similarly, the waxes are advantageously selected from among animal, fossil, plant, mineral and synthetic waxes that are per se known.

And exemplary organic solvents include the lower alcohols and polyols.

Of course, one skilled in this art will take care to select the optional additional compound(s) indicated above and/or the amounts thereof such that the advantageous properties intrinsically associated with the combination [sunscreen system+polyethylene mixture] in accordance with the invention is not, or is not substantially, adversely affected by the addition(s) envisaged.

The compositions of the invention are formulated according to techniques that are well known to this art, advantageously for the preparation of emulsions of oil-in-water (o/w) type.

For example, for the antisun/sunscreen formulations according to the invention which comprise a support of oil-in-water emulsion type, the aqueous phase (in particular comprising the hydrophilic screening agents) generally constitutes from 50% to 95% by weight, preferably from 70% to 90% by weight, relative to the total weight of the formulation, and the oily phase (in particular comprising the lipophilic screening agents) generally constitutes from 5% to 50% by weight, preferably from 10% to 30% by weight, relative to the total weight of the formulation.

In order to further illustrate the present invention and the advantages thereof, the following specific examples are given, it being understood that same are intended only as illustrative and in nowise limitative.

In said examples to follow, all parts and percentages are given by total weight, unless otherwise indicated.

EXAMPLE 1

An antisun/sunscreen formulation A according to the invention was prepared in the form of an oil-in-water type emulsion and containing:

| Formulation A | Amount (% by weight) |
| --- | --- |
| Octocrylene (Uvinul N539) | 10 |
| Octyl salicylate (Neo Heliopan OS) | 5 |
| Benzophenone-3 (Uvinul M 40) | 6 |
| 4-tert-Butyl-4'-methoxydibenzoylmethane (Parsol 1789) | 3 |
| Cyclomethicone | 7 |
| Glycols | 8 |
| Isopropyl palmitate | 2.5 |
| PVP/eicosene copolymer | 1 |
| Stearic acid | 1 |
| Dimethicone | 1 |
| Glyceryl stearate/PEG-100 stearate mixture (Arlacel 165) | 1 |
| Acrylates/$C_{10}$–$C_{30}$ alkyl acrylate crosslinked copolymer (Pemulen TR1) | 0.2 |
| Mixture of polyethylene containing a carboxylic acid end function/polyethylene of molecular weight 350, of acid number 115 and of melting point 89° C. (Performacid 350) | 2 |
| Xanthan gum | 0.1 |
| Triethanolamine | qs |
| Preservatives | qs |
| Water | qs 100 |

A comparative antisun/sunscreen formulation A' was also prepared, having the same recipe as formulation A but containing no mixture of polyethylene containing a carboxylic acid end function/polyethylene.

For each of the compositions A and A', the sun protection factor (SPF) associated therewith was then determined. This was determined employing the in vitro technique described by B. L. Diffey et al., in *J. Soc. Cosmet. Chem.*, 40, 127–133 (1989); this method entails determining the monochromatic protection factors every 5 nm over a wavelength range from 290 nm to 400 nm and in calculating therefrom the sun protection factor according to a given mathematical equation.

The results obtained (average value corresponding to five tests) are reported in Table I below:

TABLE I

| Composition | A' (comparative) without polyethylene mixture | A (invention) with polyethylene mixture |
|---|---|---|
| Average SPF (standard deviation) | 19.8 (5.1) | 31.5 (4.9) |

These results clearly evidence that the addition in an oil/water emulsion formulation of admixture of polyethylene containing a carboxylic acid endgroup/polyethylene to a sunscreen system including octocrylene, octyl salicylate, 4-tert-butyl-4'-methoxydibenzoylmethane and benzophenone-3 significantly enhances the SPF-photoprotecting values thereof.

EXAMPLE 2

An antisun/sunscreen formulation B according to the invention was prepared in the form of an emulsion of oil-in-water type and containing:

| Formulation B | Amount (% by weight) |
|---|---|
| Octocrylene (Uvinul N539) | 10 |
| Octyl salicylate (Neo Heliopan OS) | 5 |
| Benzophenone-3 (Uvinul M 40) | 6 |
| 4-tert-Butyl-4'-methoxydibenzoylmethane (Parsol 1789) | 3 |
| Glycols | 8 |
| $C_{12}$–$C_{15}$ alkyl benzoate (Finsolv TN) | 2.5 |
| PVC/eicosene copolymer | 1 |
| Stearic acid | 1 |
| Glyceryl stearate/PEG-100 stearate mixture (Arlacel 165) | 1 |
| Acrylates/$C_{10}$–$C_{30}$ alkyl acrylate crosslinked copolymer (Pemulen TR1) | 0.2 |
| Mixture of polyethylene containing a carboxylic acid end function/polyethylene of molecular weight 350, of acid number 115 and of melting point 89° C. (Performacid 350) | 0.5 |
| Xanthan gum | 0.1 |
| Triethanolamine | qs |
| Preservatives | qs |

An antisun/sunscreen formulation B' according to the invention was then also prepared, having the same recipe as formulation B but containing 2% by weight of the mixture of polyethylene containing a carboxylic acid endgroup/polyethylene.

For each of the compositions B and B', the sun protection factor (SPF) was then determined according to the same technique as in Example 1.

The results obtained (average value corresponding to five tests) are reported in Table II below:

TABLE II

| Composition | B (invention) with 0.5% of polyethylene mixture | B' (invention) with 2% of polyethylene mixture |
|---|---|---|
| Average SPF (standard deviation) | 31.3 (7.7) | 38.7 (6.5) |

These results clearly evidence that the addition in an oil/water emulsion of a mixture of polyethylene containing a carboxylic acid endgroup/polyethylene to a sunscreen system including octocrylene, octyl salicylate, 4-tert-butyl-4'-methoxydibenzoylmethane and benzophenone-3 significantly enhances the SPF-photoprotecting values thereof.

EXAMPLE 3

An antisun/sunscreen formulation C according to the invention was prepared in the form of an oil-in-water emulsion containing:

| Formulation C | Amount (% by weight) |
|---|---|
| Octocrylene (Uvinul N539) | 10 |
| 4-Methylbenzylidenecamphor (Eusolex 6300) | 4 |
| 2-Phenylbenzimidazole-5-sulfonic acid (Eusolex 232) | 1.5 |
| Benzene-1,4-bis(3-methylidene-10-camphor-sulfonic acid) (Mexoryl SX) | 1 |
| 4-tert-Butyl-4'-methoxydibenzylmethane (Parsol 1789) | 3 |
| Cyclomethicone | 7 |
| Dimethicone | 1 |
| Glycols | 8 |
| Isopropyl palmitate | 2.5 |
| PVC/eicosene copolymer | 1 |
| Stearic acid | 1 |
| Glyceryl stearate/PEG-100 stearate mixture (Arlacel 165) | 1.5 |
| Acrylates/$C_{10}$–$C_{30}$ alkyl acrylate crosslinked copolymer (Pemulen TR1) | 0.23 |
| Mixture of polyethylene containing a carboxylic acid end function/polyethylene of molecular weight 350, of acid number 115 and of melting point 89° C. (Performacid 350) | 1 |
| Xanthan gum | 0.1 |
| Triethanolamine | qs |
| Preservatives | qs |
| Water | qs 100 |

An antisun/sunscreen formulation C' according to the invention was then also prepared, having the same composition as formulation C but containing 2% by weight of a mixture of polyethylene containing a carboxylic acid end function/polyethylene.

A comparative antisun/sunscreen formulation C" was also prepared, having the same composition as formulation C but containing no mixture of polyethylene containing a carboxylic acid end function/polyethylene.

For each of the compositions C, C' and C", the sun protection factor (SPF) was then determined according to the same technique as in Example 1.

The results obtained (average value corresponding to five tests) are reported in Table III below:

TABLE III

| Composition | C" (comparative) no polyethylene mixture | C (invention) with 1% polyethylene mixture | C' (invention) with 2% polyethylene mixture |
|---|---|---|---|
| Average SPF (standard deviation) | 13.2 (2.8) | 34.6 (5.2) | 42.1 (6.7) |

These results clearly evidence that the addition in an oil/water emulsion of a mixture of polyethylene containing a carboxylic acid endgroup/polyethylene to a sunscreen system including octocrylene, 4-methylbenzylidenecamphor octyl salicylate, 4-tert-butyl-4'-methoxydibenzoylmethane, benzene-1,4-bis(3-methylidene-10-camphorsulfonic acid) and 2-phenylbenzimidazole-5-sulfonic acid significantly enhances the SPF-photoprotecting values thereof.

EXAMPLE 4

An antisun/sunscreen formulation D according to the invention was prepared in the form of an emulsion of oil-in-water type and containing:

| Formulation D | Amount (% by weight) |
|---|---|
| Octocrylene (Uvinul N539) | 10 |
| Octyl salicylate (Neo Heliopan OS) | 5 |
| Benzophenone-3 (Uvinul M 40) | 6 |
| 4-tert-Butyl-4'-methoxydibenzoylmethane (Parsol 1789) | 3 |
| Cyclomethicone | 7 |
| Glycols | 8 |
| TiO$_2$ nanopigments (MT 100T) | 3 |
| Isopropyl palmitate | 2.5 |
| PVP/eicosene copolymer | 1 |
| Stearic acid | 1 |
| Dimethicone | 1 |
| Glyceryl stearate/PEG-100 stearate mixture (Arlacel 165) | 1 |
| Acrylates/C$_{10}$–C$_{30}$ alkyl acrylate crosslinked copolymer (Pemulen TR1) | 0.2 |
| Mixture of polyethylene containing a carboxylic acid end function/polyethylene of molecular weight 350, of acid number 115 and of melting point 89° C. (Performacid 350) | 2 |
| Xanthan gum | 0.1 |
| Triethanolamine | qs |
| Preservatives | qs |
| Water | qs 100 |

A comparative antisun/sunscreen formulation D' was then also prepared, having the same composition as formulation D but containing no mixture of polyethylene containing a carboxylic acid end function/polyethylene. For each of the compositions D and D', the sun protection factor (SPF) was then determined according to the same technique as in Example 1.

The results obtained (average value corresponding to five tests) are reported in Table IV below:

TABLE IV

| Composition | D (invention) with 2% polyethylene mixture | D' (comparative) without polyethylene mixture |
|---|---|---|
| Average SPF (standard deviation) | 48.0 (11.2) | 80.5 (12.2) |

These results clearly evidence that the addition of a mixture of polyethylene containing a carboxylic acid end function/polyethylene to a sunscreen system including octocrylene, octyl salicylate, 4-tert-butyl-4'-methoxydibenzoylmethane, benzophenone-3 and TiO$_2$ significantly enhances the SPF-photoprotecting values thereof.

EXAMPLE 5

An antisun/sunscreen formulation E according to the invention was prepared in the form of an emulsion of oil-in-water type and containing:

| Formulation E | Amount (% by weight) |
|---|---|
| Octocrylene (Uvinul N539) | 10 |
| 4-tert-Butyl-4'-methoxydibenzoylmethane (Parsol 1789) | 2 |
| Benzene-1,4-bis(3-methylidene-10-camphor-sulfonic acid) (Mexoryl SX) | 2 |
| Cyclomethicone | 7 |
| Glycols | 15 |
| Isopropyl palmitate | 2.2 |
| PVC/eicosene copolymer | 1 |
| Stearic acid | 1.5 |
| Stearyl alcohol | 0.8 |
| Dimethicone | 1 |
| Glyceryl stearate/PEG-100 stearate mixture (Arlacel 165) | 1.5 |
| Acrylates/C$_{10}$–C$_{30}$ alkyl acrylate crosslinked copolymer (Pemulen TR1) | 0.2 |
| Hydroxypropylmethylcellulose | 0.1 |
| Acrylic acid crosslinked polymer (Carbomer) | 0.1 |
| Mixture of polyethylene containing a carboxylic acid end function/polyethylene of molecular weight 550, of acid number 72.5 and of melting point 101° C. (Performacid 550) | 4 |
| Xanthan gum | 0.1 |
| Triethanolamine | qs |
| Preservatives | qs |
| Water | qs 100 |

This composition had an in vitro SPF of 13.9±1.6.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition suited for improvedly UV-photoprotecting human skin and/or hair against the deleterious effects of ultraviolet irradiation, which comprises (a) an effective UV-photoprotecting amount of at least one UV-A and/or UV-B sunscreen and (b) an amount of immixture of ethylene polymers effective to enhance the SPF value of said at least one UV-A and/or UV-B sunscreen (a), said immixture of ethylene polymers (b) comprising (i) at least one carboxylated polyethylene and (ii) at least one polyethylene, formulated into a topically applicable, cosmetically/dermatologically acceptable vehicle, diluent or carrier therefor.

2. The cosmetic/dermatological UV-photoprotecting composition as defined by claim 1, said at least one carboxylated polyethylene (i) comprising an ethylene polymer having a free carboxylic acid endgroup, or a carboxylic acid endgroup optionally either partially or totally neutralized.

3. The cosmetic/dermatological UV-photoprotecting composition as defined by claim 2, comprising an oil-in-water emulsion.

4. The cosmetic/dermatological UV-photoprotecting composition as defined by claim 3, said immixture of ethylene polymers (b) comprising from about 60% to 99% by weight of said at least one carboxylated polyethylene (i) and from about 1% to 40% by weight of said at least one polyethylene (ii).

5. The cosmetic/dermatological UV-photoprotecting composition as defined by claim 4, said immixture of ethylene polymers (b) comprising from about 80% to 90% by weight of said at least one carboxylated polyethylene (i) and from about 10% to 20% by weight of said at least one polyethylene (ii).

6. The cosmetic/dermatological UV-photoprotecting composition as defined by claim 4, said immixture of ethylene polymers (b) having a number-average molecular weight ranging from about 300 to 800, an acid number ranging from about 60 to 120 and a melting point ranging from about 80° C. to 120° C.

7. The cosmetic/dermatological UV-photoprotecting composition as defined by claim 6, said immixture of ethylene polymers (b) having a molecular weight of about 350, an acid number of about 115 and a melting point of about 89° C.

8. The cosmetic/dermatological UV-photoprotecting composition as defined by claim 6, said immixture of ethylene polymers (b) having a molecular weight of about 460, an acid number of about 94 and a melting point of about 94° C.

9. The cosmetic/dermatological UV-photoprotecting composition as defined by claim 6, said immixture of ethylene polymers (b) having a molecular weight of about 550, an acid number of about 72.5 and a melting point of about 101° C.

10. The cosmetic/dermatological UV-photoprotecting composition as defined by claim 6, said immixture of ethylene polymers (b) having a molecular weight of about 700, an acid number of about 63 and a melting point of about 110° C.

11. The cosmetic/dermatological UV-photoprotecting composition as defined by claim 4, comprising from about 0.1% to 10% by weight of said immixture of ethylene polymers (b).

12. The cosmetic/dermatological UV-photoprotecting composition as defined by claim 11, comprising from about 0.2% to 5% by weight of said immixture of ethylene polymers (b).

13. The cosmetic/dermatological UV-photoprotecting composition as defined by claim 4, said at least one UV-A and/or UV-B sunscreen (a) comprising at least one hydrophilic organic UV-screening agent and/or at least one lipophilic organic UV-screening agent and/or at least one mineral UV-screening (nano)pigment.

14. The cosmetic/dermatological UV-photoprotecting composition as defined by claim 13, said at least one UV-A and/or UV-B sunscreen (a) comprising a cinnamic compound, a dibenzoylmethane compound, a salicylic compound, a camphor compound, a triazine compound, a benzophenone compound, a β,β'-diphenylacrylate compound, a benzimidazole compound, a bis-benzazolyl compound, a bis-hydroxyphenolbenzotriazole compound, a p-aminobenzoic acid compound, a UV-screening hydrocarbyl polymer and/or a UV-screening silicone.

15. The cosmetic/dermatological UV-photoprotecting composition as defined by claim 14, said at least one UV-A and/or UV-B sunscreen (a) comprising benzene-1,4-bis(3-methylidene-10-camphorsulfonic acid) and/or 2-phenylbenzimidazole-5-sulfonic acid.

16. The cosmetic/dermatological UV-photoprotecting composition as defined by claim 14, said at least one UV-A and/or UV-B sunscreen (a) comprising 4-tert-butyl-4'-methoxydibenzoylmethane, octyl methoxycinnamate, 2-ethylhexyl α-cyano-β,β-diphenylacrylate (octocrylene), 4-methylbenzylidenecamphor, benzophenone-3 (oxybenzone), 2-ethylhexyl salicylate or octyl salicylate, 2,4,6-tris[p-(2'-ethylhexyl-1'-oxycarbonyl)-anilino]-1,3,5-triazine, and/or drometrizole trisiloxane.

17. The cosmetic/dermatological UV-photoprotecting composition as defined by claim 13, said at least one UV-A and/or UV-B sunscreen (a) comprising a coated or uncoated metal oxide (nano)pigment.

18. The cosmetic/dermatological UV-photoprotecting composition as defined by claim 17, said coated or uncoated metal oxide (nano)pigment comprising titanium dioxide, zinc oxide, iron oxide, zirconium oxide and/or cerium oxide.

19. The cosmetic/dermatological UV-photoprotecting composition as defined by claim 13, comprising from about 0.1% to 30% by weight of said least one UV-A and/or UV-B sunscreen (a).

20. The cosmetic/dermatological UV-photoprotecting composition as defined by claim 19, comprising from about 0.5% to 15% by weight of said least one UV-A and/or UV-B sunscreen (a).

21. The cosmetic/dermatological UV-photoprotecting composition as defined by claim 3, further comprising an effective amount of at least one artificial/sunless tanning and/or bronzing agent.

22. The cosmetic/dermatological UV-photoprotecting composition as defined by claim 3, further comprising at least one fatty substance, organic solvent, thickener, softener, opacifier, stabilizer, colorant, emollient, antifoam, moisturizer, fragrance, preservative, polymer, filler, sequestering agent, bactericide and/or odor absorber, acidifying or basifying agent, surfactant, free-radical scavenger, antioxidant, vitamin, α-hydroxy acid, or mixture thereof.

23. A regime/regimen for improvedly UV-photoprotecting human skin and/or hair against the deleterious effects of ultraviolet irradiation, comprising topically applying thereon (a) an effective UV-photoprotecting amount of at least one UV-A and/or UV-B sunscreen and (b) an amount of immixture of ethylene polymers effective to enhance the SPF value of said at least one UV-A and/or UV-B sunscreen (a), said immixture of ethylene polymers (b) comprising (i) at least one carboxylated polyethylene and (ii) at least one polyethylene, formulated into a topically applicable, cosmetically/dermatologically acceptable vehicle, diluent or carrier therefor.

24. A regime/regimen for improvedly UV-photoprotecting human skin and/or hair against the deleterious effects of ultraviolet irradiation, comprising topically applying thereon a topically applicable cosmetically/dermatologically acceptable oil-in-water emulsion which comprises (a) an effective UV-photoprotecting amount of at least one UV-A and/or UV-B sunscreen and (b) an amount of immixture of ethylene polymers effective to enhance the SPF value of said at least one UV-A and/or UV-B sunscreen (a), said immixture of ethylene polymers (b) comprising (i) at least one carboxylated polyethylene and (ii) at least one polyethylene.

25. The UV-photoprotecting regime/regimen as defined by claim 24, said at least one carboxylated polyethylene (i) comprising an ethylene polymer having a free carboxylic acid endgroup, or a carboxylic acid endgroup optionally either partially or totally neutralized.

26. A method for enhancing the SPF-value of at least one UV-A and/or UV-B sunscreen in UV-photoprotecting cosmetic/dermatological compositions comprised thereof, which comprises admixing and intimately formulating therewith, in a topically applicable, cosmetically/dermatologically acceptable oil-in-water emulsion comprised thereof, an amount of immixture of ethylene polymers effective to enhance the SPF value of said at least one UV-A and/or UV-B sunscreen, said immixture of ethylene polymers comprising (i) at least one carboxylated polyethylene and (ii) at least one polyethylene.

* * * * *